United States Patent [19]

Bennett

[11] Patent Number: 4,595,684

[45] Date of Patent: Jun. 17, 1986

[54] METHOD OF SUPPRESSING BENZODIAZEPINE INDUCED SEDATION WITH 2-(p-METHOXYPENYL)-PYRAZOLO[4,3-c]QUINOLIN-3(5H)-ONE OR A SALT THEREOF

[75] Inventor: Debra A. Bennett, Middlesex, N.J.

[73] Assignee: Ciba-Geigy Corporation, Ardsley, N.Y.

[21] Appl. No.: 766,868

[22] Filed: Aug. 16, 1985

[51] Int. Cl.[4] .............................................. A61K 31/55
[52] U.S. Cl. ................................................... 514/221
[58] Field of Search ........................................ 514/221

[56] References Cited

U.S. PATENT DOCUMENTS 4,312,870  1/1982  Yokoyama ........................ 514/293

Primary Examiner—Stanley J. Friedman
Attorney, Agent, or Firm—Michael W. Glynn; Irving M. Fishman

[57] ABSTRACT

A method of suppressing benzodiazepine induced sedation normally associated in the treatment of anxiety in a mammal with an anxiolytically effective amount of a benzodiazepine anti-anxiety agent, comprising the administration to said mammal an effective sedation antagonistic amount of 2-(p-methoxyphenyl)-pyrazolo[4,3-c]quinolin-3(5H)-one or a pharmaceutically acceptable salt thereof.

6 Claims, No Drawings

METHOD OF SUPPRESSING BENZODIAZEPINE INDUCED SEDATION WITH 2-(p-METHOXYPENYL)-PYRAZOLO[4,3-c] QUINOLIN-3(5H)-ONE OR A SALT THEREOF

BACKGROUND OF THE INVENTION

Benzodiazepine anxiolytic agents constitute a well known class of psychoactive agents useful in the treatment of anxiety. Such agents include diazepam, bromazepam, alprazolam, camazepam, clobazam, chlordesmethyldiazepam, clorazepate, halazepam, prazepam, lorazepam, chlordiazepoxide, oxazepam, flurazepam and the like. Unfortunately, conventional benzodiazepine anxiolytic agents also possess sedative and muscle relaxant side effects, which may result in fatigue, drowsiness, diminished mental alertness, or ataxia.

2-Aryl-pyrazolo[4,3-c]quinolin-3-ones, including 2-(p-methoxyphenyl)-pyrazolo[4,3-c]quinolin-3(5H)-one, pharmaceutically acceptable salts thereof, and their use as psychoactive agents in the treatment of anxiety or depression are described in U.S. Pat. No. 4,312,870.

SUMMARY OF THE INVENTION

The present invention concerns the discovery that 2-(p-methoxyphenyl)-pyrazolo[4,3-c]quinolin-3(5H)-one, and the pharmaceutically acceptable salts thereof, surprisingly and unexpectedly selectively antagonize the sedative effect of benzodiazepine anxiolytic agents, without substantially reducing the desired anxiolytic effect.

Accordingly it is an object of the present invention to provide a method of suppressing benzodiazepine induced sedation normally associated in the treatment of anxiety with a benzodiazepine anxiolytic agent, by the administration of an effective sedation antagonistic amount of 2-(p-methoxyphenyl)-pyrazolo[4,3-c]quinolin-3(5H)-one or a pharmaceutical acceptable salt thereof.

It is a further objective of the present invention to provide a method of treating anxiety in a mammal, by administering to said mammal an anxiolytically effective amount of a benzodiazepine anxiolytic agent in combination with an effective amount, to suppress attendant benzodiazepine induced sedation, of 2-(p-methoxyphenyl)pyrazolo[4,3-c]quinolin-3(5H)-one or a pharmaceutically acceptable salt thereof.

It is yet a further object of the instant invention to provide pharmaceutical compositions containing a combination of an anxiolytically effective amount of benzodiazepine anxiolytic agent and an effective amount, to suppress attendant benzodiazepine induced sedation, of 2-(-methoxyphenyl)-pyrazolo[4,3-c]quinolin-3(5H)-one, or a pharmaceutically acceptable salt thereof, alone or in further combination with conventional pharmaceutical excipients.

DETAILED DESCRIPTION OF THE INVENTION

One embodiment of the invention comprises a method of suppressing, in a mammal, benzodiazepine induced sedation of the type associated in the treatment of anxiety with an anxiolytically effective amount of a benzodiazepine anxiolytic agent, by the administration to said mammal of an effective sedation antagonistic amount of 2-(p-methoxyphenyl)-pyrazolo[4,3-c]quinolin-3(5H)-one, or a pharmaceutically acceptable salt thereof.

Representative benzodiazepine anxiolytic agents for use in the practice of the instant invention constitute a well known class of anxiolytic agents, and include, without limitation, those of the formula

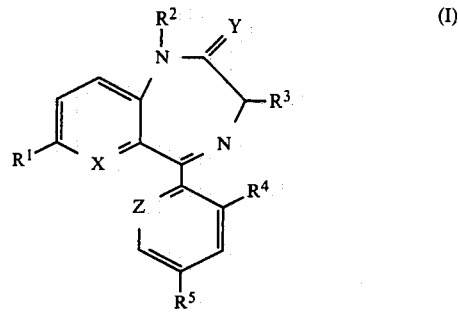

wherein $R^1$ is chloro; nitro; or bromo;

$R^2$ is hydrogen; methyl; 2,2,2-trifluoroethyl; cyclopropylmethyl; N,N-diethylaminoethyl; isothiocyanatoethyl; ethynyl; or bromomethyl carbonylaminoethyl, $R^3$ is hydrogen; hydroxy; carboxy; N,N-dimethylcarbamoyloxy; or carboethoxy;

$R^4$ is hydrogen; chloro; or fluoro;

$R^5$ is hydrogen or chloro;

X is N or CH;

Y is O or S;

Z is N or CH;

or a pharmaceutically acceptable salt thereof.

Benzodiazepines according to Formula I are enumerated, for example in Annual Reports of Medicinal Chemistry, Vol. 15, p.23(1980); Vol. 16, p.32 (1981); Vol. 17, p. 13 (1982) and Vol. 19, p. 12 (1984).

Pharmaceutically acceptable salts of 2-(p-methoxyphenyl)-pyrazolo[4,3-c]quinolin-3(5H)-one, and benzodiazepines, such as those of formula I, include salts of pharmaceutically acceptable inorganic and organic acids, such as strong metalloidic acids, for example hydrohalic, e.g. hydrochloric or hydrobromic acid; sulfuric, phosphoric, or nitric acid; and aliphatic or aromatic carboxylic or sulfonic acids, e.g. formic, acetic, propionic, succinic, glycollic, lactic, malic, tartaric, citric, ascorbic, maleic, pyruvic, phenylacetic, benzoic, 4-aminobenzoic, anthranilic, 4-hydroxybenzoic, salicylic, methanesulfonic, ethanesulfonic, hydroxyethanesulfonic, toluenesulfonic, sulfanilic or cyclohexylsulfamic acid.

Pharmaceutically acceptable salts of the compounds of formula I, where $R^3$ is carboxy, include salts of pharmaceutically acceptable organic and inorganic bases, such as the alkali metal and alkaline earth metal salts, especially the sodium and potassium salts, ammonium salts and salts of amines, including lower alkylated amines, such as methylamine, ethylamine, trimethylamine and the like, hydroxyloweralkylamines, such as ethanolamine and diethanolamine, and heterocyclic amines, such as morpholine and piperazine.

A related embodiment comprises the treatment of anxiety in a mammal in the need of such treatment by administering to said mammal an anxiolytically effective amount of a benzodiazepine anxiolytic agent in combination with an effective amount, to suppress attendant benzodiazepine induced sedation, of 2-(p-methoxyphenyl)pyrazolo[4,3-c]quinolin-3(5H)-one, or a pharmaceutically accepted salt thereof.

The selective antagonism of the sedative effect of benzoidazepines by the administration of an effective amount of 2-(p-methoxyphenyl)-pyrazolo[4,3-c]quinolin-3(5H)-one, or salt thereof, can be demonstrated in the Rat Rotorod Performance test. In this test, the 2-(p-methoxyphenyl)-pyrazolo[4,3-c]quinolin-3(5H)-one is administered orally to Wistar rats (130-160 g) 30 minutes prior to receiving a 30 mg/kg intraperitoneal dose of the subject benzodiazepine and 30 minutes following the benzodiazepine injection, the subject rat is evaluated in the Rat Rotorod Performance test. Rotorod performance is assessed using a conventional rotored apparatus modified by placing a section of polyethylene material over the drum. The rat is placed on the drum, which is rotated at a speed of 16 rpm, and required to remain on the drum for 16 seconds. Each animal is allowed three trials to reach the criterion. Any animal that fails to reach this criterion is considered to have a performance deficit. The performance is then compared with the performance of Wistar rats receiving the benzodiazepine dose alone.

For example, a 30 mg/kg dose of diazepam alone reliably impairs rotorod performance, as diazepam induces the deficit with an $ED_{50}$ value of about 13.6(11.2–16.4) mg/kg. In the above test, the $ED_{50}$ amount of 2-(p-methoxyphenyl)-pyrazolo[4,3-c]quinolin-3(5H)-one sufficient to antagonize the rotorod deficit induced by diazepam is about 1.36 (1.06–1.83) mg/kg. The 2-(p-methoxyphenyl)-pyrazolo[4,3-c]quinolin-3(5H)-one by itself produces no impairment of rotorod behavior even at doses of up to 100 mg/kg, in comparison to control activity. Surprisingly, the antagonism of the rotorod deficit induced by diazepam cannot be attributed to a blockage of the anxiolytic activity of diazepam because the subject compound, 2-(p-methoxyphenyl)-pyrazolo-[4,3c]quinolin3(5H)-one, does not significantly antagonize the anticonflict effect of diazepam, as shown for example, by the administration of the subject compound (30 mg/kg.) orally to Wistar rats (300–350 g) 30 minutes prior to the intraperitioneal administration of diazepam (at 3 and 10 mg/ky) and behavioral testing, using a behavioral conflict paradigm as described in U.S. Pat. No. 4,312,870, col. 3, lines 2–28.

Weight ratios of the subject compound, 2-(p-methoxyphenyl)-pyrazolo[4,3-c]quinolin-3(5H)-one or a pharmaceutically acceptable salt thereof, to the benzo-diazepine anxiolytic agent, useful in selectively antagonizing the sedative effect of the benzodiazepine are generally between about 0.2 to about 20, preferably between about 0.5 to about 10 mg per mg benzodiazepine component. The applied dosage of each of the two components will, in part, depend on the nature of the benzodiazepine component, but will generally range between about 0.01 and 10 mg/kg/day, preferably between about 0.02 and 5 mg/kg/day, advantageously between about 0.05 and 1 mg/kg/day.

The 2-(p-methoxyphenyl)-pyrazolo[4,3-c]quinolin-3(5H)-one component may be administered to the mammalian host, e.g. mice, rats, monkeys, humans, either prior to, simultaneously with, or subsequent to, the administration of the benzodiazepine component. Each of the two components may independently be administered enterally, parenterally, advantageously orally, or subcutaneously, intravenously or intraperitonally. Preferably, the sedation antagonistic component is administered prior to, e.g. up to six hours prior to, or simultaneously with, the benzodiazepine component. When administered simultaneously, it is convenient to have both components formulated together into unit dosage forms.

Pharmaceutical compositions can be formulated containing each of the components, or both, containing an effective amount thereof in conjunction or admixture with excipients suitable for either enteral or parenteral administration. Preferred are tablets and gelatin capsules comprising the active ingredients together with (a) diluents, e.g. lactose, dextrose, sucrose, mannitol, sorbitol, cellulose, and/or glycine, (b) lubricants, e.g. silica, talcum, stearic acid, its magnesium salt and/or polyethylene-glycol, for tablets (c) binders, e.g. magnesium aluminum silicate, starch paste, gelatin, traganth, methylcellulose, and/or polyvinylpyrrolidone, if desired (d) disintegrants, e.g. starches, agar, alginic acid or its sodium salt, enzymes of the binders or effervescent mixtures and/or (e) absorbants, colorants, flavors and sweeteners. Injectable compositions are preferably aqueous isotonic solutions or suspensions and suppositories are advantageously made from fatty emulsions or suspensions. They may also contain other therapeutically valuable substances. Said pharmaceutical compositions are prepared according to conventional mixing, granulating or coating methods respectively and contain about 0.1 to 75%, preferably about 1 to 50% of the two active ingredients.

The following examples, illustrating the invention, are not to be construed as being limitations thereon.

EXAMPLE 1

Preparation of 10,000 capsules each containing 2 mg diazepam and 10 mg 2-(p-methoxyphenyl)-pyrazolo[4,3-c]quinolin-3(5H)-one:

Formula:

2-(p-methoxyphenyl)-pyrazolo[4,3-c]quinolin-3(5H)-one—100 g
diazepam—20 g
lactose—1,780 g
talcum powder—100 g

PROCEDURE

All of the powders are passed through a screen with openings of 0.6 mm. Then the drug substances are placed in a suitable mixer and mixed first with the talcum, then with the lactose until homogeneous. No. 3 capsules are filled with 200 mg each, using a capsule filling machine.

EXAMPLE 2

The procedure and formation specifics of Example 1 are followed, substituting 20 g lorazepam for the diazepam component.

EXAMPLE 3

The procedure and formulation specifics of Example 1 are followed, substituting 100 g prazepam for the diazepam component, and using 1700 g lactose.

EXAMPLE 4

The procedure and formulation specifics of Example 1 are followed, substituting 100 g halazepam for the diazepam component, and using 1700 g lactose.

EXAMPLE 5

The procedure and formulation specifics of Example 1 are followed substituting 20 g of oxazepam for the diazepam component.

EXAMPLE 6

The procedure and formulation specifics of Example 1 are followed, substituting chloroazepate dipotassium (20 g) for the diazepam component.

EXAMPLE 7

The procedure and formulation specifics of Example 1 are followed, substituting 50 g of chlordiazepoxide for the diazepam component, and using 1,750 g lactose.

What is claimed:

1. A method of suppressing benzodiazepine induced sedation of the type normally associated in the treatment of anxiety in a mammal receiving anxiolytically effective amount of a benzodiazepine anxiolytic agent, comprising the administration to said mammal of an effective sedation antagonistic amount of 2-(p-methoxyphenyl)-pyrazolo[4,3-c]quinolin-b 3(5H)-one or a pharmaceutically acceptable salt thereof.

2. A method according to claim 1, wherein said benzodiazepine anxiolytic agent is selected from the group consisting of diazepam, bromazepam, alprazolam, camazepam, clobazam, chlordesmethyldiazepam, clorazepate, halazepam, prazepam, lorazepam, chlorodiazepoxide, oxazepam and flurazepam.

3. A method according to claim 1 wherein said benzodiazepine is diazepam.

4. A method according to claim 1 wherein the administration of the benzodiazepine anxiolytic agent is substantially simultaneous with the administration of 2-(p-methoxyphenyl)-pyrazolo[4,3-c]quinolin-3(5H)-one, or a pharmaceutically acceptable salt thereof.

5. A method according to claim 4, wherein said simultaneous administration is as a unit dose form.

6. A method according to claim 5, wherein said simultaneous administration is oral.

* * * * *